US012723828B2

(12) United States Patent
Yollu et al.

(10) Patent No.: US 12,723,828 B2
(45) Date of Patent: Sep. 1, 2026

(54) MECHANISM DISASSEMBLY DEVICE FOR WEAPONS WITH BOLT MECHANISM

(71) Applicant: ATA SILAH SANAYI ANONIM SIRKETI, Istanbul (TR)

(72) Inventors: Fatih Yollu, Istanbul (TR); Cem Gultekin, Istanbul (TR)

( * ) Notice: Subject to any disclaimer, the term of this patent is extended or adjusted under 35 U.S.C. 154(b) by 128 days.

(21) Appl. No.: 18/849,705

(22) PCT Filed: Feb. 13, 2024

(86) PCT No.: PCT/TR2024/050112

§ 371 (c)(1),
(2) Date: Sep. 23, 2024

(87) PCT Pub. No.: WO2025/085011

PCT Pub. Date: Apr. 24, 2025

(65) Prior Publication Data

US 2026/0177336 A1 Jun. 25, 2026

(51) Int. Cl.

| | |
|---|---|
| ***F41A 17/36*** | (2006.01) |
| ***F41A 3/22*** | (2006.01) |
| ***F41A 3/72*** | (2006.01) |
| ***F41A 11/00*** | (2006.01) |
| ***F41A 11/02*** | (2006.01) |
| ***F41A 17/42*** | (2006.01) |
| ***F41A 17/54*** | (2006.01) |

(Continued)

(52) U.S. Cl.

CPC ................ *F41A 17/42* (2013.01); *F41A 3/22* (2013.01); *F41A 3/72* (2013.01); *F41A 11/00* (2013.01); *F41A 11/02* (2013.01); *F41A 17/54* (2013.01); *F41A 17/56* (2013.01); *F41A 19/10* (2013.01); *F41A 19/46* (2013.01); *A61B 2090/0813* (2016.02)

(58) Field of Classification Search

CPC .... F41A 17/42; F41A 3/22; F41A 3/18; F41A 3/20; F41A 3/72; F41A 11/00; F41A 11/02; F41A 17/54; F41A 17/56; F41A 17/36; F41A 19/10; F41A 19/46

See application file for complete search history.

(56) References Cited

U.S. PATENT DOCUMENTS 5,520,019 A * 5/1996 Schuetz .................... F41A 3/54
89/197
5,718,073 A * 2/1998 Sachse ................ H05B 39/088
89/1.3

(Continued)

FOREIGN PATENT DOCUMENTS

| | | |
|---|---|---|
| TR | 2020/14025 U | 12/2021 |
| TR | 2022/003506 U | 3/2022 |
| TR | 2023/004056 U | 4/2023 |

OTHER PUBLICATIONS

International Search Report for corresponding PCT/TR2024/050112, dated May 17, 2024.

(Continued)

*Primary Examiner* — Michael D David
(74) *Attorney, Agent, or Firm* — EGBERT, MCDANIEL & SWARTZ, PLLC

(57) ABSTRACT

Disclosed is a mechanism disassembly device for weapons with a bolt mechanism, which allows the mechanisms to be removed and installed from the body with one hand, without a button.

4 Claims, 2 Drawing Sheets

(51) Int. Cl.
*F41A 17/56* (2006.01)
*F41A 19/10* (2006.01)
*F41A 19/46* (2006.01)
*A61B 90/00* (2016.01)

(56) References Cited

U.S. PATENT DOCUMENTS

| | | | | |
|---|---|---|---|---|
| 8,333,137 | B2 * | 12/2012 | Sirochman | F41A 9/38 89/1.4 |
| 9,488,423 | B2 * | 11/2016 | Sullivan | F41A 13/12 |
| 10,605,553 | B1 * | 3/2020 | Collazo | F41C 7/00 |
| 12,474,134 | B2 * | 11/2025 | Köysüren | F41A 17/36 |
| 2012/0180648 | A1 * | 7/2012 | Sullivan | F41A 13/12 89/193 |
| 2019/0078849 | A1 | 3/2019 | Schafer | |
| 2021/0381784 | A1 | 12/2021 | Alomaira | |
| 2022/0163275 | A1 | 5/2022 | Ballard et al. | |
| 2024/0361093 | A1 * | 10/2024 | Hubbell | F41A 3/72 |

OTHER PUBLICATIONS

Written Opinion of the International Searching Authority for corresponding PCT/TR2024/050112, dated May 17, 2024.

* cited by examiner

MECHANISM DISASSEMBLY DEVICE FOR WEAPONS WITH BOLT MECHANISM

TECHNICAL FIELD

The invention relates to a mechanism disassembly device for weapons with bolt mechanism.

The invention is especially related to the mechanism disassembly device for with bolt mechanism, which allows the mechanisms to be removed and installed from the body with one hand, without a button.

BACKGROUND OF THE INVENTION

Firearms such as pistols and rifles are known to be frequently used in the hunting and defense industries.

It is very important that the mentioned weapons be disassembled quickly in the field and reassembled quickly when needed.

Users can only perform the disassembly and reassembly operations mentioned with auxiliary tools or apparatus. To achieve this goal, users have to carry tools and apparatus with them.

In bolt-action rifles, mechanism fixing parts are used to prevent the mechanism working inside the body from moving out of place due to undesirable reasons, to stop it in the rearmost position, to ensure that it is locked and unlocked at a certain angle, and to support its linear movement.

To disassemble the mechanism group, in many firearms, this button (fixing part) located on the edge of the body is pressed and removed by pulling the mechanism with the other hand.

In designs where this button is not available (where the sled function for the mechanism is assigned to another part), buttons are placed in different positions but with the same functions and perform the same function.

In currently used systems, in order to remove the mechanism from the body, it is necessary to hold and pull the mechanism with one hand while pressing the button with the other hand. This is an uncomfortable and difficult application for users.

Since current working systems work like lever systems, problems such as stripping and dislocation of the part holding the mechanism in the opposite direction of the pressure of the spring used are encountered.

In the literature, in the utility model application numbered TR 2020 14025 in the records of the Turkish Patent and Trademark Office, it is stated that "The invention is used on the firing mechanism with a mechanism body attached to the winding rifles to ensure the explosion of the cartridge when the rifle trigger is pulled, and to make the rifle ready for shooting by installing the firing mechanism. It is related to the winding handle, which is positioned inside the mechanism body to ensure the movement and contains a ring-shaped foot surrounding its entire surface. Feature of the invention; It contains a side wall in the form of an outward protrusion, which is located on the edge surface of the winding handle and ensures that the winding handle gets stuck in the movement body by turning half a turn when the winding handle makes a turning movement." statements are included.

In the said application, the structure located on the edge surface of the crown, which ensures that the crown is stuck by turning half a turn within the movement body when the crown makes a turning movement, is disclosed.

Again, in the literature, in the records of the Turkish Patent and Trademark Office, in the utility model application numbered TR 2023 004056, it is stated that "Our invention; It is used in all rifled and smoothbore rifles and is related to the firing mechanism on the upper body of the gun and the mechanisms to feed the cartridge into the barrel. The cocking handle must be pulled back in order to take a cartridge into the firing mechanism and insert it into the barrel. When the crown is pulled back, the helical slotted cylinder moves backwards and the helical slot on it moves the resting head of the rotation shaft, which is fixed to the rotation guide inner shaft, until it rests on the rotation shaft by rotating on its own axis. In this way, the need to close it by turning it downwards after pulling the crown is eliminated. After this stage, the cock required for the needle to hit the cartridge igniter is pulled back with the finger. This tensile force trigger mechanism is activated when pulled, causing the hammer to hit the needle and the needle to hit the cartridge igniter in the barrel, thus igniting the cartridge." statements are included.

In the mentioned application, the rifle bolt mechanism that rotates within the mechanism with the horizontal movement of the cocking handle is disclosed.

Again, in the literature, in the utility model application numbered TR 2022 003506 in the records of the Turkish Patent and Trademark Office, it is stated that "The invention is about a cocking handle and its cocking mechanism developed for use in bolt action-straight pull model firearms." In order to fulfill this, the invention branch; The installation mechanism, which is the subject of the invention, is assembled by placing it perpendicular to the mechanism body and rotating it, using the tight fitting principle. It contains the said winding lever, bolt mechanism, lever pin, lever spring, spring fixing pin, case and at least one channel positioned on this case, in which the winding lever operates." statements are included.

In the mentioned utility model, a cocking handle for firearms and its cocking mechanism are disclosed.

Due to the disadvantages mentioned above, there was a need to introduce a mechanism disassembly device for weapons with bolt mechanism.

DISCLOSURE OF THE INVENTION

Based on this state of the art, the aim of the invention is to provide a mechanism disassembly device for weapons with bolt mechanism that eliminates the existing disadvantages.

Another aim of the invention is to provide a structure that prevents the mechanism working inside the body from being displaced due to undesirable reasons.

Another aim of the invention is to create a structure that allows the user to remove the mechanism from the body with one hand, without using a button when disassembling the mechanism.

Another aim of the invention is to provide a structure that is easier to use than the old spring system and prevents the spring from deforming compared to the springs in traditional systems.

Another aim of the invention is to create a structure that prevents undesirable situations such as stripping of the mechanism holder or getting loose from the mechanism, and therefore increases its service life, since the spring works in the center of the mechanism holder.

REFERENCE NUMBERS

1. Mechanism Holder Cover
2. Mechanism Holder
3. Mechanism Holder Spring
4. Mechanism Holder Cover Spring
5. Body Group
6. Mechanism Group
7. Stock Group

DETAIL DESCRIPTION OF THE INVENTION

In this detailed explanation, the innovation that is the subject of the invention is explained only with examples that will not create any limiting effect for a better understanding of the subject.

The invention a mechanism disassembly device for weapons with bolt mechanism which allows the mechanisms to be removed and installed from the body with one hand without a button and which consists of at least one body group (5) located on the upper side of the weapon, at least one mechanism group (6) formed as the said bolt mechanism, and at least one stock group (7), characterized in that comprises, crown mounted on the mechanism group (6) which is turned counterclockwise and pulled up to the last fixing stage in order to remove the said mechanism group (6), mechanism holder (2) which enables the mechanism group (6) to come out of the body group (5) by getting rid of the ramp formed on the said mechanism group (6).

Figure 1:
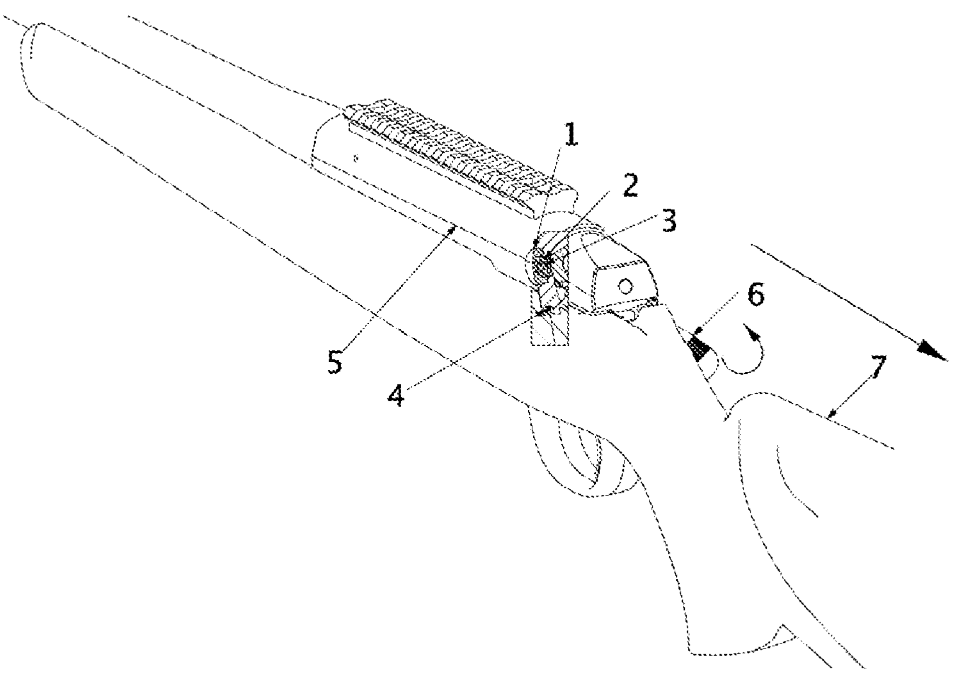
FIG. 1 A perspective view of the mechanism disassembly device for weapons with bolt mechanism that are the subject of the invention FIG. 2 Another perspective view of the mechanism disassembly device for the weapons with bolt mechanism that are the subject of the invention FIG. 3 Another perspective view of the mechanism disassembly device for weapons with bolt mechanism that are the subject of the invention

FIG. 1 shows a perspective view of the mechanism disassembly device for weapons with bolt mechanism that are the subject of the invention.

Figure 2:
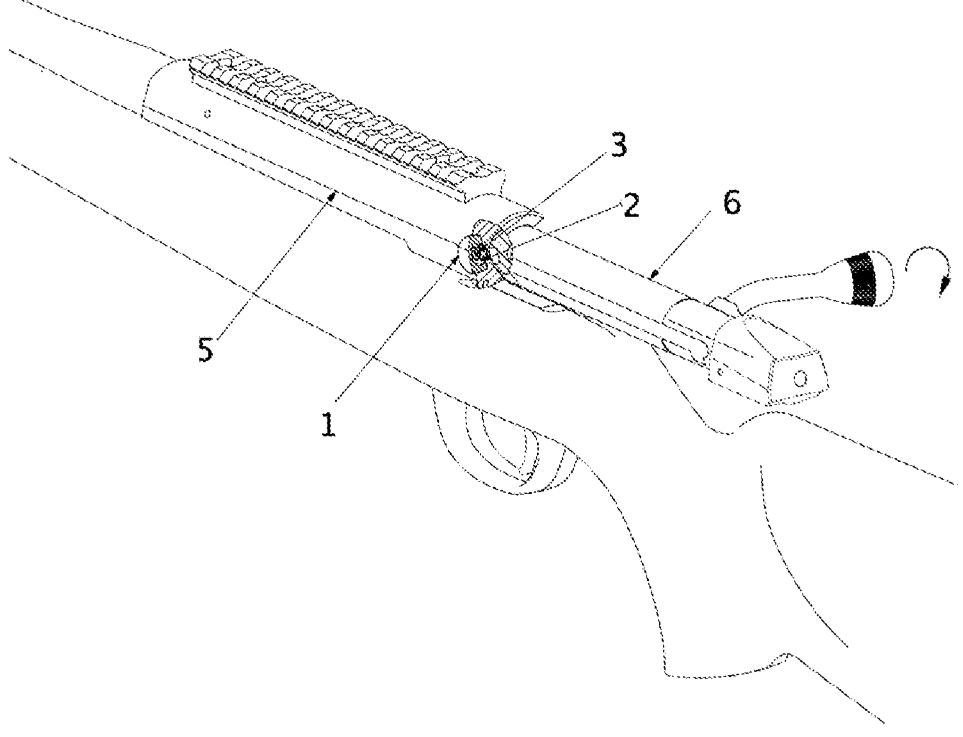

FIG. 2 shows another perspective view of the mechanism disassembly device for the weapons with bolt mechanism that are the subject of the invention.

Figure 3:
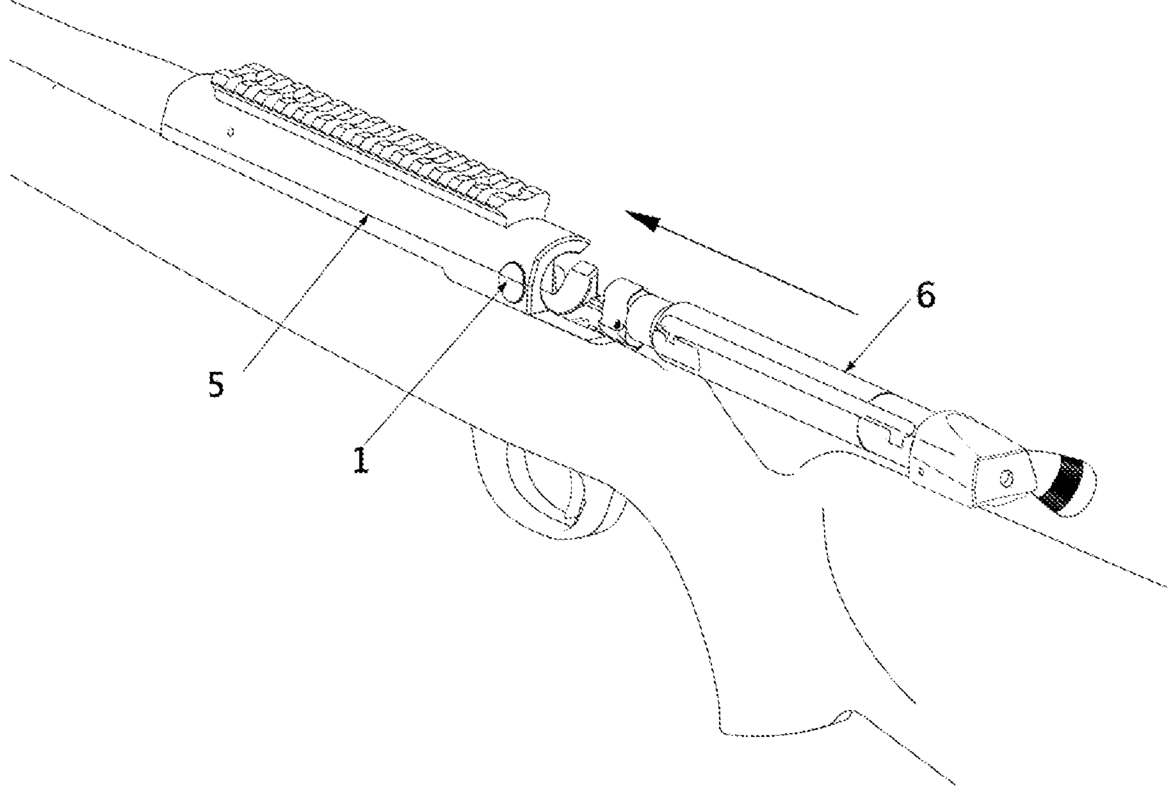

FIG. 3 shows another perspective view of the mechanism disassembly device for weapons with bolt mechanism that are the subject of the invention.

The mechanism disassembly device that is the subject of the invention consists main parts of; the body group (5) located on the upper side of the weapon, the mechanism group (6) formed as the said bolt mechanism, the mechanism holder (2) which allows the mechanism group (6) to come out of the body group (5) by getting rid of the ramp formed on the said mechanism group (6), mechanism holder cover (1), which is opened on the said body group (5) and positioned as the cover of the said mechanism holder (2), the mechanism holder spring (3), which allows the mechanism group (6) to be placed in its position within the body group (5) by moving it into the body group (5) and creating pressure on it, thanks to the ramp on the mechanism group (6), the mechanism holder cover spring (4), which enables the said mechanism holder cover (1) to be opened and closed, and the stock group (7).

To remove the mechanism group (6) mentioned in FIG. 1, the crown mounted on the mechanism group (6) is turned counterclockwise (in the direction of the arrow) and pulled in the direction of the arrow to the last fixing stage.

In FIG. 2, when the mechanism group (6) is rotated clockwise (arrow direction), thanks to the form on the mechanism group (6), the mechanism is released from the ramp on the holder (2) and comes out of the body group (5).

In FIG. 3, the mechanism group (6) is moved into the body group (5) thanks to the ramp on it, and by pressing the mechanism holder spring (3) working inside the mechanism holder (2), the mechanism group (6) is moved to its position within the body group (5) is becoming established.

The invention claimed is:

1. A mechanism disassembly device for a weapon with a bolt mechanism which allows the mechanisms to be removed and installed from a body of the weapon with one hand without a button and which comprises at least one body group located on an upper side of the weapon, at least one mechanism group formed as the said bolt mechanism, and at least one stock group, a crown mounted on the mechanism group is turned counterclockwise and pulled up in order to remove the said mechanism group, and a mechanism holder which enables the mechanism group to come out of the body group by disengaging from the ramp formed on the said mechanism group.

2. A mechanism disassembly device for weapons according to claim 1, comprising a mechanism holder spring, which allows the mechanism group to be placed in its position within the body group by moving it into the body group and creating pressure on it, due to the ramp on the mechanism group.

3. A mechanism disassembly device for weapons according to claim 1, comprising a mechanism holder cover, which is opened on the said body group and positioned as the cover of the said mechanism holder.

4. A mechanism disassembly device for weapons according to claim 3, comprising a mechanism holder cover spring, which enables the said mechanism holder cover (H) to be opened and closed.

* * * * *